(12) United States Patent
Dunlavey

(10) Patent No.: US 6,985,846 B1
(45) Date of Patent: Jan. 10, 2006

(54) SYSTEM AND METHOD FOR SIMULATING CLINICAL TRIAL PROTOCOLS WITH COMPILED STATE MACHINES

(75) Inventor: Michael R. Dunlavey, Needham, MA (US)

(73) Assignee: Pharsight Corporation, Mountain View, CA (US)

( * ) Notice: Subject to any disclaimer, the term of this patent is extended or adjusted under 35 U.S.C. 154(b) by 807 days.

(21) Appl. No.: 09/823,213

(22) Filed: Mar. 30, 2001

Related U.S. Application Data

(60) Provisional application No. 60/265,710, filed on Jan. 31, 2001.

(51) Int. Cl.
G06F 9/45 (2006.01)

(52) U.S. Cl. ............................. 703/22; 705/2; 717/136

(58) Field of Classification Search .................. 703/11, 703/22; 705/2; 700/83; 701/216; 717/106, 717/136; 716/4; 714/10; 715/501.1
See application file for complete search history.

(56) References Cited

U.S. PATENT DOCUMENTS

| | | | |
|---|---|---|---|
| 5,808,918 A * | 9/1998 | Fink et al. ..................... 703/11 |
| 6,051,029 A | 4/2000 | Paterson et al. | |
| 6,069,629 A | 5/2000 | Paterson et al. | |
| 6,078,738 A | 6/2000 | Garza et al. | |
| 6,108,635 A * | 8/2000 | Herren et al. .................. 705/2 |
| 6,268,853 B1 * | 7/2001 | Hoskins et al. ............... 700/83 |
| 6,408,431 B1 * | 6/2002 | Heughebaert et al. ...... 717/106 |
| 6,651,225 B1 * | 11/2003 | Lin et al. ........................ 716/4 |
| 6,708,329 B1 * | 3/2004 | Whitehill et al. ........... 717/136 |
| 6,735,523 B1 * | 5/2004 | Lin et al. .................... 701/216 |
| 6,820,235 B1 * | 11/2004 | Bleicher et al. ......... 715/501.1 |
| 6,823,471 B1 * | 11/2004 | Arimilli et al. ............... 714/10 |

OTHER PUBLICATIONS

Michael R. Dunlavey, Performance Tuning: Slugging It Out!, Dr. Dobb's Journal, Nov. 1993.
Michael R. Dunlavey, Differential Evaluation: a Cache-based Technique for Incremental Update of Graphical Display of Structures, Software Practice and Experience, vol. 23, No. 8, Aug. 1993, pp 871-893 (Wiley).
High Performance System, Inc., http://www.hps-inc.com/index.html, Mar. 2001.

* cited by examiner

Primary Examiner—Paul L. Rodriguez
Assistant Examiner—Kandasamy Thangavelu
(74) Attorney, Agent, or Firm—Townsend and Townsend and Crew LLP

(57) ABSTRACT

A system and method for simulating clinical trial protocols with compiled state machines is presented. The system receives input data representing a clinical trial protocol. This information is sorted into a plurality of schedules, including dosage schedules, observation schedules, and various other types of schedules. The schedules are translated into a general purpose high level programming language and then compiled into and executable file. The executable file may comprise a plurality of discrete state machines, each state machine corresponding directly to a single schedule. During the clinical trial simulation, the executable file is run by the trial simulator to simulate the trial protocol.

20 Claims, 9 Drawing Sheets

SYSTEM AND METHOD FOR SIMULATING CLINICAL TRIAL PROTOCOLS WITH COMPILED STATE MACHINES

RELATED APPLICATION

The present application claims priority to U.S. provisional patent application Ser. No. 60/265,710 entitled SYSTEM AND METHOD FOR SIMULATING CLINICAL TRIALS WITH COMPILED STATE MACHINES, filed on Jan. 31, 2001, which is hereby incorporated by reference in its entirety.

BACKGROUND OF THE INVENTION

1. Field of the Invention

The present invention relates generally to the field of clinical trials, and more specifically to computer aided simulation of clinical drug trials using compiled state machines.

2. Related Art

The need for clinical drug trials has spawned a sophisticated industry of software designers who create clinical trial simulation applications that run thousands of clinical trial simulations. These trial simulations allow drug manufacturers to simulate how well their products may fare in the very rigorous, extremely expensive, and mandatory FDA clinical drug testing trials. Simulating clinical drug trials using computers vastly reduces the costs associated with bringing a potential product to the clinical trial phase while significantly increasing the potential for success in the clinical trial phase.

The simulation of a clinical trial requires a drug model that provides the data necessary to simulate the behavior of the drug in the body of a living organism. Additionally, a clinical trial simulation requires a trial protocol that provides the dosage and observations schedules for the trial. The dosage schedule indicates when drug treatments are to be given to the individual subjects and how much of the drug is to be administered. The observation schedule indicates what observations or measurements are to be taken of the subject and at what times. In a single trial, there can be multiple dosage schedules and multiple observation schedules.

For example, in simulating clinical trials it is necessary to simulate each individual subject. The simulation of an individual subject requires simulating the time sequence of the various independent dosing and observation schedules. Furthermore, schedules must be capable of dynamic modification during the trial in order to simulate dose adjustment protocols that respond to factors in the trial such as disease progress.

Conventional clinical trial simulators typically meet these requirements by accepting the drug model and trial protocol as input and then interpreting the input to simulate the trial. FIG. 1 is a block diagram illustrating a prior art clinical trial simulator system 5. Simulator 5 has a controller 10, an interface 15, an interpreter 20 and a data storage area 25. Generally, controller 10 executes and controls the operation of interface 15 to elicit the necessary drug model and trial protocol as operational data that is input into the simulator 5. The operational data (e.g. the drug model and trial protocol) is usually stored in data storage area 25.

Once the necessary operational data has been collected, controller 10 begins the simulation and instructs interpreter 20 to begin interpreting the trial protocol and the drug model in order to sequentially simulate each subject in the simulation. One conventional method for running a trial simulation is to compute each schedule before the subject begins. This pre-determined schedules can then be saved in data storage area 25. The multitude of saved schedules are then combined into a single master schedule which is then followed by controller 10 for the entire simulation. This conventional solution lacks the flexibility to modify any schedule in response to data generated during the simulation, as is required for dose adjustment protocols.

Another conventional method for running a trial simulation is to represent each of the multitude of schedules as tabular data in data storage area 25. Controller 10 then examines each schedule, in turn, to determine the next action to be taken in the simulation. This conventional solution also lacks flexibility and additionally lacks performance. The lack of performance is due to the significant amount of time required to continuously examine each of the multitude of schedules that are part of the trial. The lack of flexibility arises from the difficulty of designing an instruction set for the simulation that adequately anticipates all possible future requirements for complex schedules.

Yet another conventional method for running a trial simulation is to represent each of the multitude of schedules as an independent ad-hoc program thread. In such a conventional method, each thread is created for a specific schedule and can only carry out that schedule. The various threads are executed in parallel by controller 10 and synchronized in order to simulate the combined course of activities relevant to the particular subject being simulated. This approach suffers from poor availability and reliability of multi-thread support in certain software environments. Additionally, multi-thread applications are difficult to debug and validate in a preemptive multitasking environment.

Therefore, the state of the art has created a need for a system and method that overcomes these significant problems found in the conventional systems as described above.

SUMMARY OF THE INVENTION

The present invention is directed to systems and methods for simulating clinical trial protocols using compiled state machines. The schedules are translated into a general purpose high level programming language and then compiled into and executable file containing machine code. The executable file may comprise a plurality of discrete state machines, each state machine corresponding directly to a single schedule. During the clinical trial simulation, the executable file containing machine code is run by the trial simulator.

In one embodiment, a system receives, as input, data representing a clinical trial protocol. This information is sorted into a plurality of schedules. The schedules can include dosage schedules, observation schedules, and various other types of schedules. Other and further aspects and features of the invention will become apparent from the following drawings and detailed description.

BRIEF DESCRIPTION OF THE DRAWINGS

Aspects and features of the described embodiments are illustrated by way of example, and not by way of limitation, in the figures of the accompanying drawings, in which like reference numerals refer to like components, and in which.

DETAILED DESCRIPTION OF THE INVENTION

Certain embodiments of the invention are now disclosed and described herein, and are directed to systems and methods for simulating clinical trials using compiled state machines. For example, one method disclosed herein allows for state machines to be created for each schedule in a clinical trial. The state machines are then compiled executed as machine code on the simulation computer, providing for faster, more flexible simulation of clinical trials.

After reading this description it will become apparent to those skilled in the art how to implement aspects and features of the invention in various alternative embodiments and alternative applications that are contemplated within the scope of the invention. Although various embodiments of the invention are described herein, it is understood that these embodiments are presented by way of example only, and not limitation. As such, this detailed description of various alternative embodiments should not be construed to limit the scope or breadth of the invention, as set forth in the appended claims.

Figure 1:
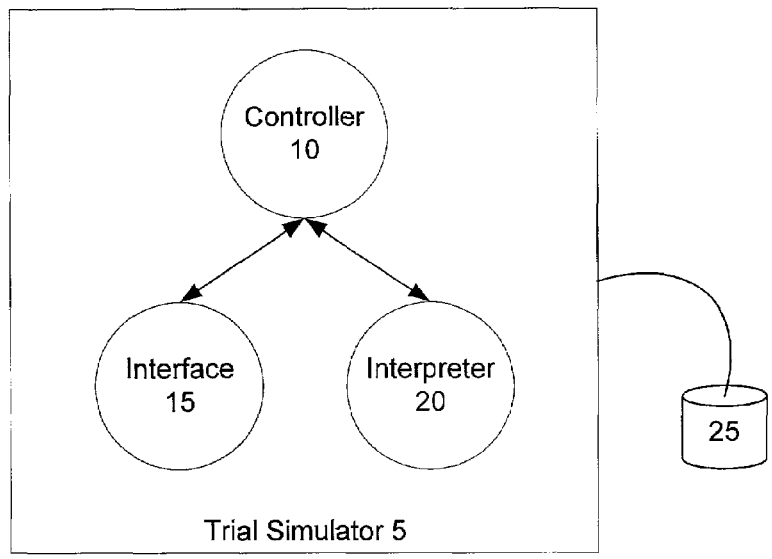
FIG. 1 is a block diagram illustrating a prior art clinical trial simulator system.
Figure 2:
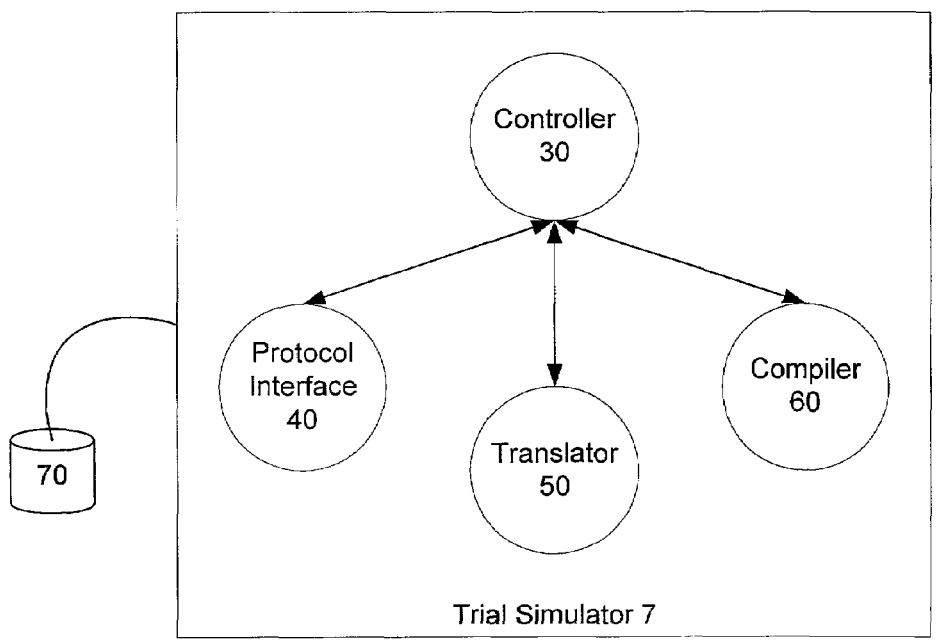
FIG. 2 is a block diagram illustrating an overview of a clinical trial simulator system according to an embodiment of the present invention.

FIG. 2 is a block diagram illustrating an overview of a clinical trial simulator 7 according to an embodiment of the present invention. Simulator 7 may comprise a controller 30, a protocol interface 40, a translator 50, and a compiler 60. Preferably, simulator 7 is communicatively coupled with a data storage area 70. Data storage area 70 can reside on a volatile or persistent storage device. For example, data storage area 70 can be a traditional database, a hard drive with a file system, a volatile memory, a persistent memory, or various other types of storage devices or structures capable of temporarily or persistently storing information.

Controller 30 preferably manages a clinical trial simulation by executing the various modules that comprise the simulator 7. For example, controller 30 can initiate protocol interface 40, translator 50, compiler 60, and other aspects of a clinical trail simulation as needed to carry out the simulation.

Protocol interface 40 can be a programmable software module that manages the graphical user interface ("GUI") of simulator 7 and presents the various data collection and presentation screens to an operator and accepts any input from the operator. Input provided to simulator 7 through protocol interface 40 can advantageously include a trial protocol and a drug model for a clinical drug trial simulation.

Translator 50 preferably performs the function of converting a clinical trial protocol into source code. Advantageously, the source code generated by translator 50 may be in any general purpose high level programming language.

Compiler 60 preferably compiles the source code generated by translator 50 into a machine code executable file that is run by controller 30 as part of the clinical trial simulation.

The controller manages the other modules and the process of obtaining the operational data from the user/operator, translating the operational data into source code, compiling the source code into machine code, and executing the machine code during the trial simulation.

Figure 3:
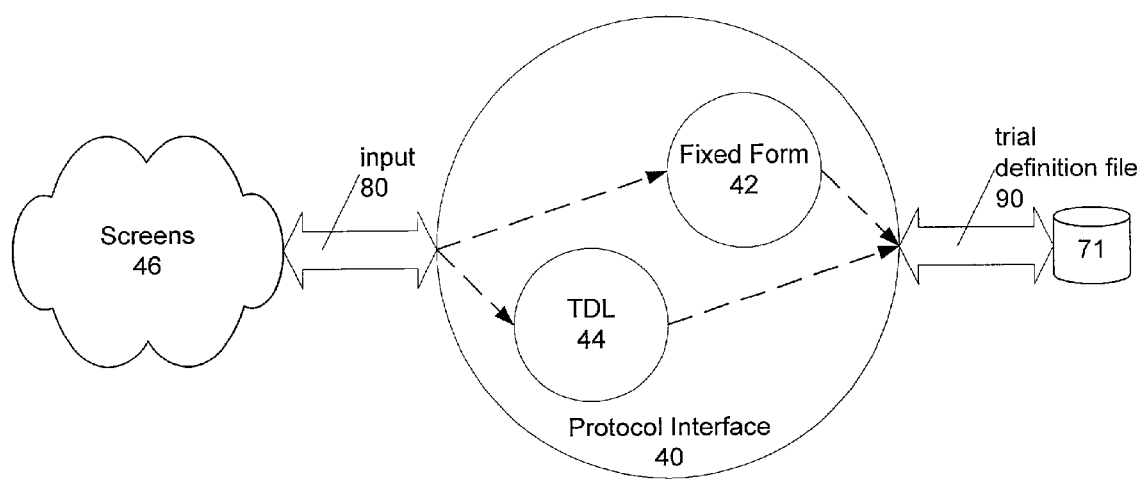
FIG. 3 is a flow diagram illustrating the operation of an interface module in a clinical trial simulator according to an embodiment of the present invention.

FIG. 3 is a flow diagram illustrating the operation of protocol interface 40 in a clinical trial simulator according to an embodiment of the present invention. Protocol interface 40 may comprise a fixed form module 42 and a trial design language ("TDL") module 44. Preferably, protocol interface 40 presents a series of screens 46 to an operator and collects certain data pertaining to the trial protocol as input 80.

The input 80 may be collected through a series of screens 46 that are in a fixed format. Advantageously, fixed form module 42 may manage the collection of input 80 in a fixed format. Additionally, fixed form module 42 may also save the data it collects in data storage area 71 as a trial definition file 90.

Similarly, TDL module 44 may collect input 80 through one or more free form entry screens that allows an operator to enter text that may advantageously conform to a predefined format such as a structured language designed for clinical trial simulators. Additionally, TDL module 44 may save the data it collects in data storage area 71 as part of the same trial definition file 90. Advantageously, between fixed form module 42 and TDL module 44, protocol interface 40 can collect all of the data needed to create the trial protocol schedules needed to run a clinical drug trial.

Figure 3A:
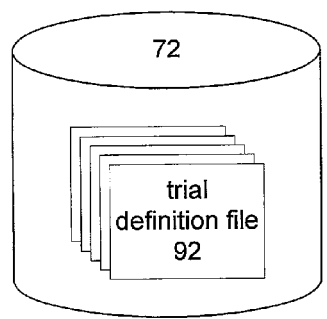
FIG. 3A is a block diagram illustrating an example trial definition file located in a data storage area according to an embodiment of the present invention.

FIG. 3A is a block diagram illustrating an example trial definition file 92 located in data storage area 72 according to an embodiment of the present invention. Trial definition file 92 preferably contains each of the various schedules that comprise the defined clinical drug trial. For example, a single clinical trial may include a dosing schedule and an observation schedule. Each of these schedules are preferably contained in trial definition file 92.

Figure 3B:
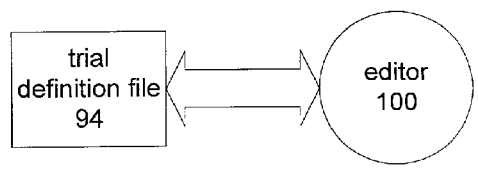
FIG. 3B is a block diagram illustrating an example editor modifying a trial definition file in a clinical trial simulator according to an embodiment of the present invention.

FIG. 3B is a block diagram illustrating an example editor 100 modifying a trial definition file 94 according to an embodiment of the present invention. In one embodiment, trial definition file 94 may be represented in various formats. For example, trial definition file 94 may be in binary format or text format. Additionally, trial definition file may be in a combination format. Editor 100 preferably can read the various types of formats for trial definition file 94 and allows an operator to edit the data that is contained in trial definition file 94. Advantageously, editor 100 allows an operator to modify certain characteristics of a dosage schedule, observation schedule, or other type of trial protocol data without employing protocol interface 40.

Figure 4:
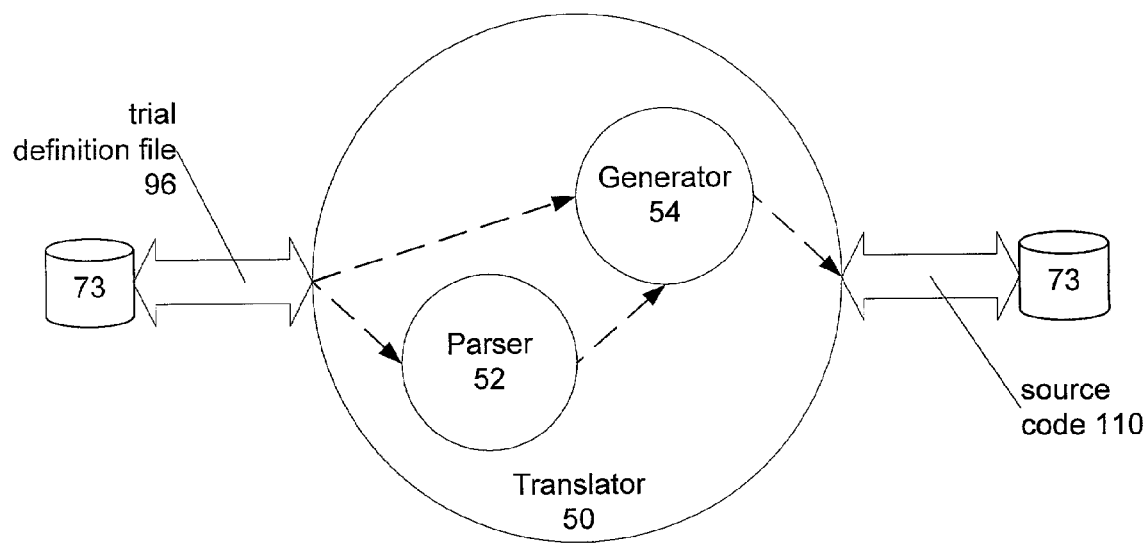
FIG. 4 is a flow diagram illustrating the operation of a translator module in a clinical trial simulator according to an embodiment of the present invention.

FIG. 4 is a flow diagram illustrating the operation of translator module 50 in a clinical trial simulator according to an embodiment of the present invention. Translator 50 may comprise a parser 52 and a generator 54. Additionally, translator 54 preferably retrieves trial definition file 96 from data storage area 73 and translates the file into source code 110, that is also stored in data storage area 73.

For example, translator 50 may retrieve trial definition file 96 from data storage area 73. Upon retrieving the file, parser 52 may analyze the file to determine its syntax and structural components and convert the data into an intermediate format. Subsequently, parser 52 may pass the intermediate format data to generator 54.

Generator 54 preferably generates source code in a high level general purpose programming language that corresponds to the trial definition file 96 and the intermediate format data received from parser 52. Furthermore, translator 54 preferably creates a separate source code file for each schedule that is defined in trial definition file 96.

Alternatively, for certain portions of the data in trial definition file 96 that were created using fixed form module 42 of the protocol interface 40, the syntax and structure of the data may advantageously already be known. In such a case, the parsing step of parser 52 can be eliminated and generator 54 can generate high level general purpose programming language source code directly from the data in trial definition file 96.

Figure 4A:
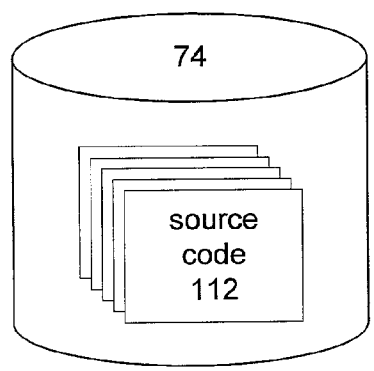
FIG. 4A is a block diagram illustrating an example set of source code files located in a data storage area according to an embodiment of the present invention.

FIG. 4A is a block diagram illustrating an example set of source code files 112 located in data storage area 74 according to an embodiment of the present invention. Source code 112 may comprise a plurality of separate source code files, although each file is preferably associated with the same clinical trial simulation. In one embodiment, a plurality of sets of source code 112 can be stored in data storage area 74, each set of source code 112 corresponding to a different trial simulation.

Figure 5:
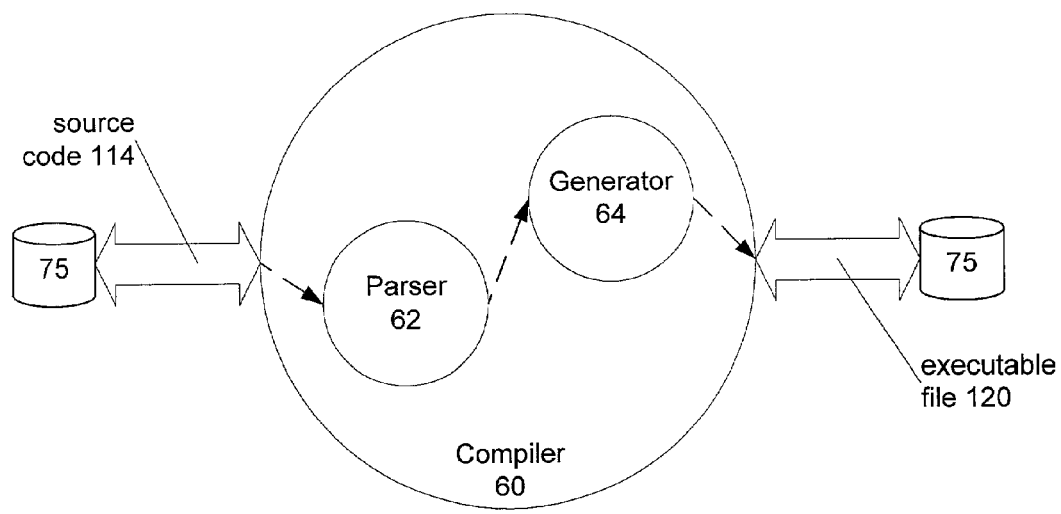
FIG. 5 is a flow diagram illustrating the operation of a compiler module in a clinical trial simulator according to an embodiment of the present invention.

FIG. 5 is a flow diagram illustrating the operation of a compiler module 60 in a clinical trial simulator according to an embodiment of the present invention. Compiler module 60 may comprise a parser 62 and a generator 64. In general, compilers are well known in the art and therefore the compiler module will not be described in further detail.

The function of compiler module 60 is preferably to read in source code 114 from data storage area 75 and produce an executable file 120 that is also stored in data storage area 120. Preferably, executable file 120 is created in machine code that corresponds to the particular computer hardware (as later described with reference to FIG. 12) that is running the trial simulator.

Figure 5A:
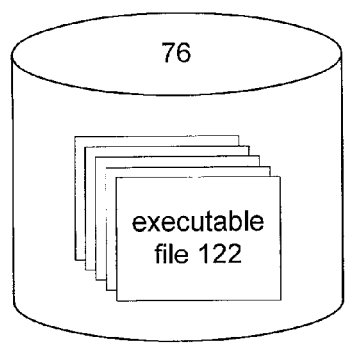
FIG. 5A is a block diagram illustrating an example executable program located in persistent storage according to an embodiment of the present invention.

FIG. 5A is a block diagram illustrating an example executable file 122 located in data storage area 76 according to an embodiment of the present invention. As illustrated, a plurality of executable files 122 may be co-located in data storage area 76. In one embodiment, each executable file 122 in data storage area 76 may correspond to a separate clinical trial simulation.

Figure 5B:
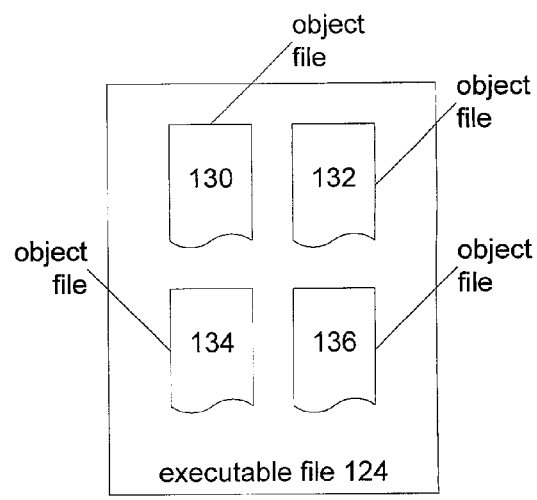
FIG. 5B is a block diagram illustrating an example executable program file according to an embodiment of the present invention.

FIG. 5B is a block diagram illustrating an example executable program file 124 according to an embodiment of the present invention. In one embodiment, executable file 124 may comprise a plurality of object files 130, 132, 134, and 136. Advantageously, each object file may correspond to a single source code file, which in turn corresponds to a single schedule in the trial protocol. Preferably, compiler 60 links each of the object files together into a single executable file 124 that can be run by controller 30 when executing the clinical trial simulation.

Figure 6:
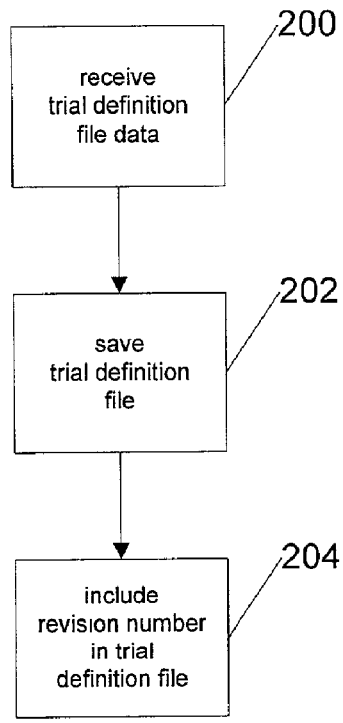
FIG. 6 is a flowchart illustrating an example process for creating a trial definition file through an interface according to an embodiment of the present invention.

FIG. 6 is a flowchart illustrating an example process for creating a trial definition file through an interface according to an embodiment of the present invention. Initially, in step 200, the simulator receives the data that constitutes the trial definition file. This data may be received in a rigid format, for example through a fixed format module, or the data may be received in a less rigid format such as a structured TDL.

Once all of the dosage, observation, and other schedules that make up the data that constitutes the trial definition file have been received, the trial definition file is preferably saved in a persistent data storage area, as illustrated in step 202. Advantageously, as shown in step 204, a revision number or some other indicator can be saved as part of the trial definition file in order to flag or track when the file is edited and when the file is in sync with its corresponding source code files, and vice-versa.

Figure 7:
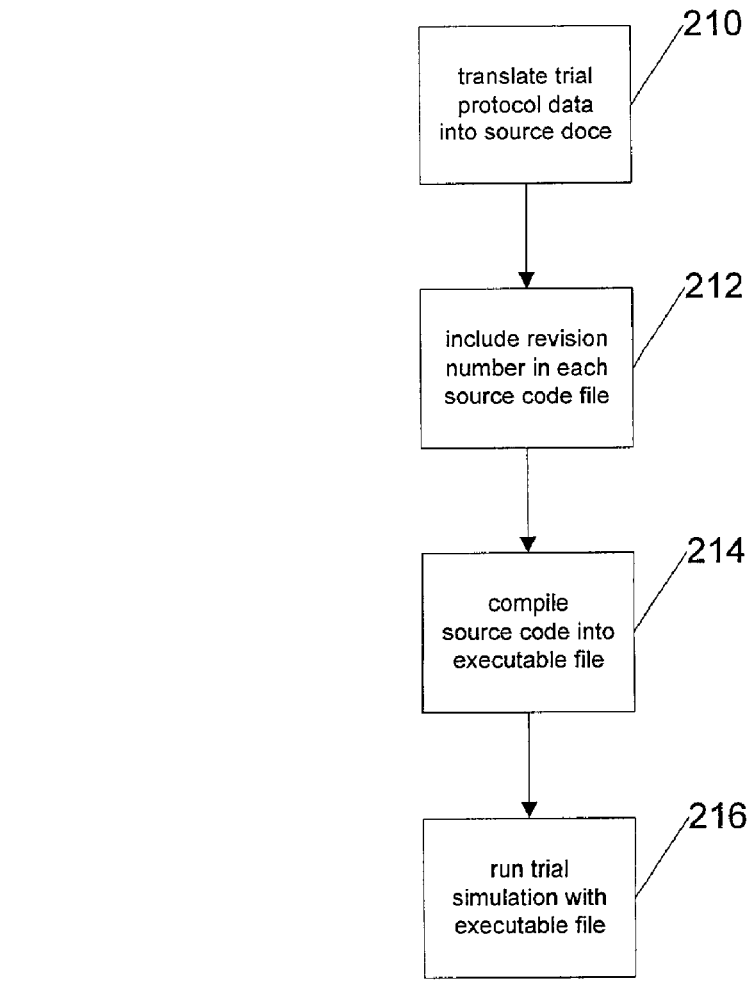
FIG. 7 is a flowchart illustrating an example overview process for running a clinical trial simulation according to an embodiment of the present invention.

FIG. 7 is a flowchart illustrating an example overview process for running a clinical trial simulation according to an embodiment of the present invention. To begin this process, the trial definition file is preferably already open (step not shown). In step 210, the simulation controller preferably calls the translator to translate the trial protocol data from the trial definition file into source code. The source code can be in any high level general purpose programming language. In one embodiment, the translator generates Fortran source code from the schedules contained in the trial protocol.

As with the creation of the trial definition file, the translator preferably includes a revision number or other indicator can be included in the source code files that correspond to the schedules for the simulation, as illustrated in step 212. In one embodiment, the revision number can be included in each source code file as a comment at the beginning of the file. Subsequently, the source code files can be compiled together into an executable file, as shown in step 214. Once the source code has been compiled, the trial simulation can be run with the executable file, as seen in step 216.

Figure 8:
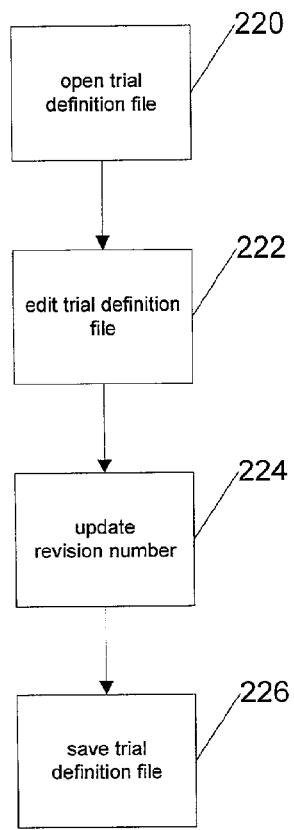
FIG. 8 is a flowchart illustrating an example process for editing a trial definition file according to an embodiment of the present invention.

FIG. 8 is a flowchart illustrating an example process for editing a trial definition file according to an embodiment of the present invention. Initially, in step 220 an existing trial definition file is opened. Preferably, the file can be opened through the protocol interface. Alternatively, the file can be opened through an editor capable of reading the format of the trial definition file. In one embodiment, an editor capable of reading the format of the trial definition file is also capable of updating the revision number or other indicator contained within the file.

Once the file has been successfully opened, the trial definition file can be edited, as illustrated in step 222. The editing may take place through a rigid interface such as the fixed format module or the editing may take place through a less formal interface such as the TDL module. Furthermore, the editing may take place through a very unstructured interface as may be provided by an alternative editor. After the file has been edited, the revision number is preferably updated to indicate that the file has been modified, as seen in step 224. Advantageously, this step may take place immediately before saving and closing the trial definition file, as shown in step 226.

Figure 9:
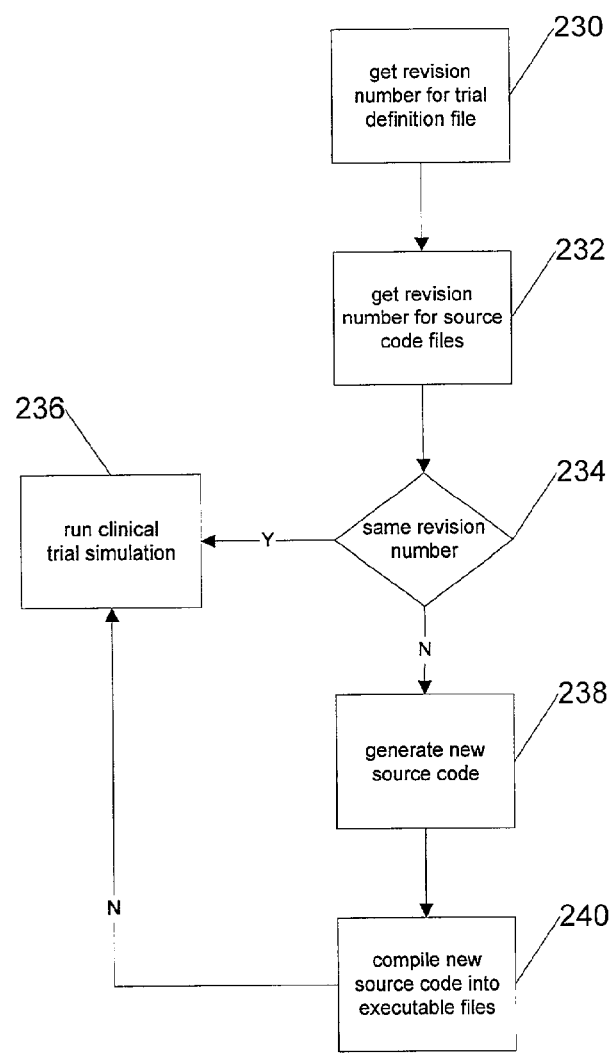
FIG. 9 is a flowchart illustrating an example process for running a clinical trial simulation an additional time according to an embodiment of the present invention.

FIG. 9 is a flowchart illustrating an example process for running a clinical trial simulation an additional time according to an embodiment of the present invention. To begin, the trial definition file is opened (step not shown). Initially, in step 230, the revision number or other indicator for the trial definition file is determined. Next, in step 232, the revision number or other indicator for each source code file is determined. In step 234, a comparison of the revision numbers or other indicators is made to determine if the source code files are still in sync with the trial definition file. If the revision number or other indicators match, the clinical trial simulation is executed, as illustrated in step 236.

If the revision numbers or other indicators do not match, new source code is generated for the trial definition file, as shown in step 238. Once the new source code is generated, the source code is preferably compiled, as illustrated in step 240. After the new source code is compiled into a new executable file, the clinical trial simulation can be executed, as seen in step 236.

Figure 10:
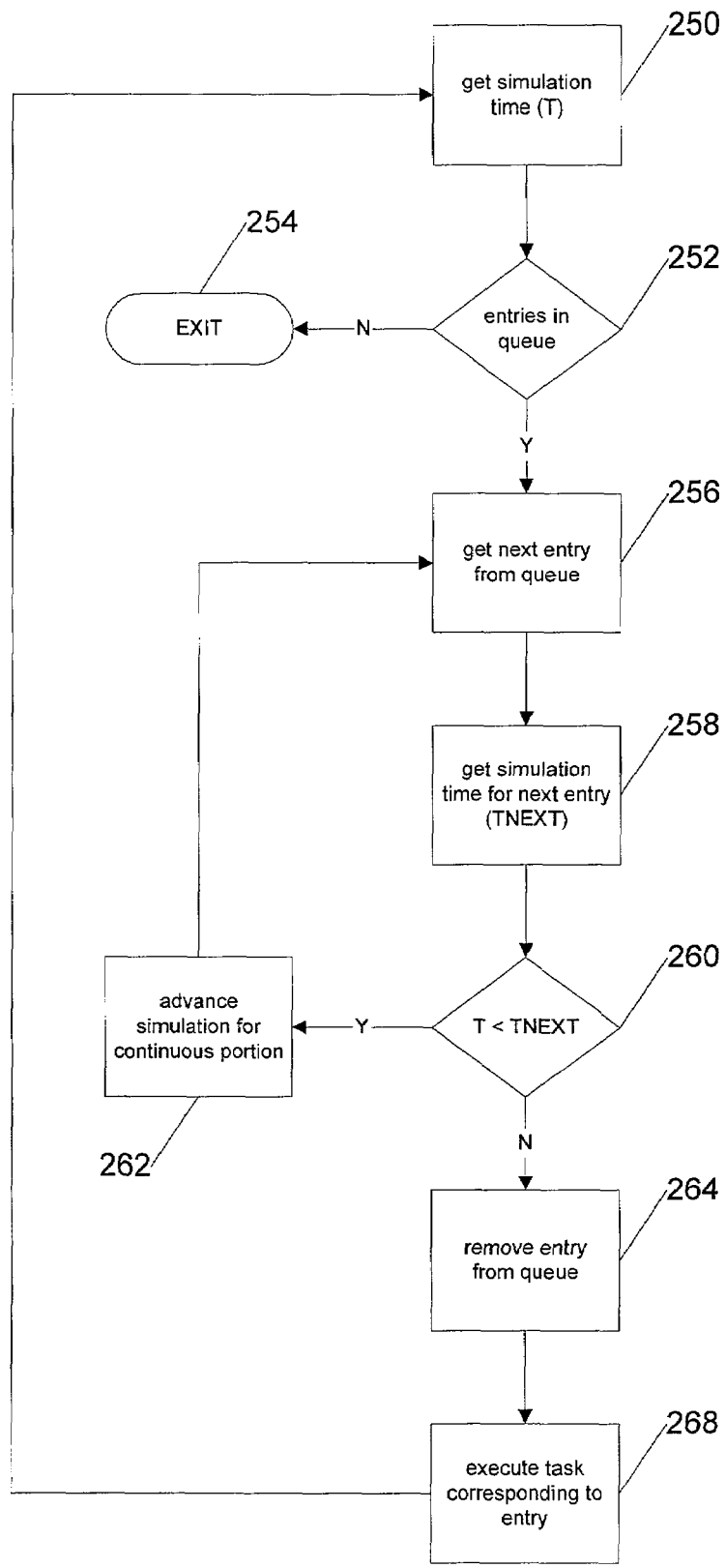
FIG. 10 is a flowchart illustrating an example process for controlling a clinical trial simulation according to an embodiment of the present invention.

FIG. 10 is a flowchart illustrating an example process for controlling a clinical trial simulation according to an embodiment of the present invention. Initially, in step 250, the controller gets the current simulation time. The current simulation time can be referred to as T. Once the current simulation time (T) has been obtained, the controller checks the operational queue to see if there are any waiting tasks, as shown in step 252. If no tasks are waiting in the queue, then the simulation is complete and the controller can exit, as seen in step 254.

If there are tasks waiting in the queue, then the controller gets the next entry from the queue, as illustrated in step 256. Preferably, the next entry in the queue is the entry with the earliest simulation time, relative to all of the entries in the queue. In step 258, the controller gets the simulation time for the previously obtained next entry. This simulation time for the next entry in the queue can be referred to as TNEXT.

In step 260, the current simulation time T is compared to the simulation time for the next entry TNEXT. If the current simulation time (T) is less than the simulation time for the next entry (TNEXT), the controller preferably advances the simulation for the continuous portions of the simulation, as described in step 262. Such a process for a controller (advancing continuous simulation when no current simulation time (T) entry is available in the queue) is well known in the art and will therefore not be described in detail in the present application. Once the continuous simulation has been advanced and T has been increased to TNEXT, the controller returns to step 256 and gets the next entry from the queue. Typically this would be the same entry as previously retrieved from the queue.

On the other hand, in step 260, if the current simulation time T is compared to the simulation time for the next entry TNEXT and the current simulation time (T) is equal to the simulation time for the next entry (TNEXT), the controller preferably removes the entry from the queue, as shown in step 264, and executes the task associated with the entry, as illustrated in step 268. Upon executing the task, the controller returns to step 250 and obtains the current simulation time in order to continue running the simulation.

Figure 11:
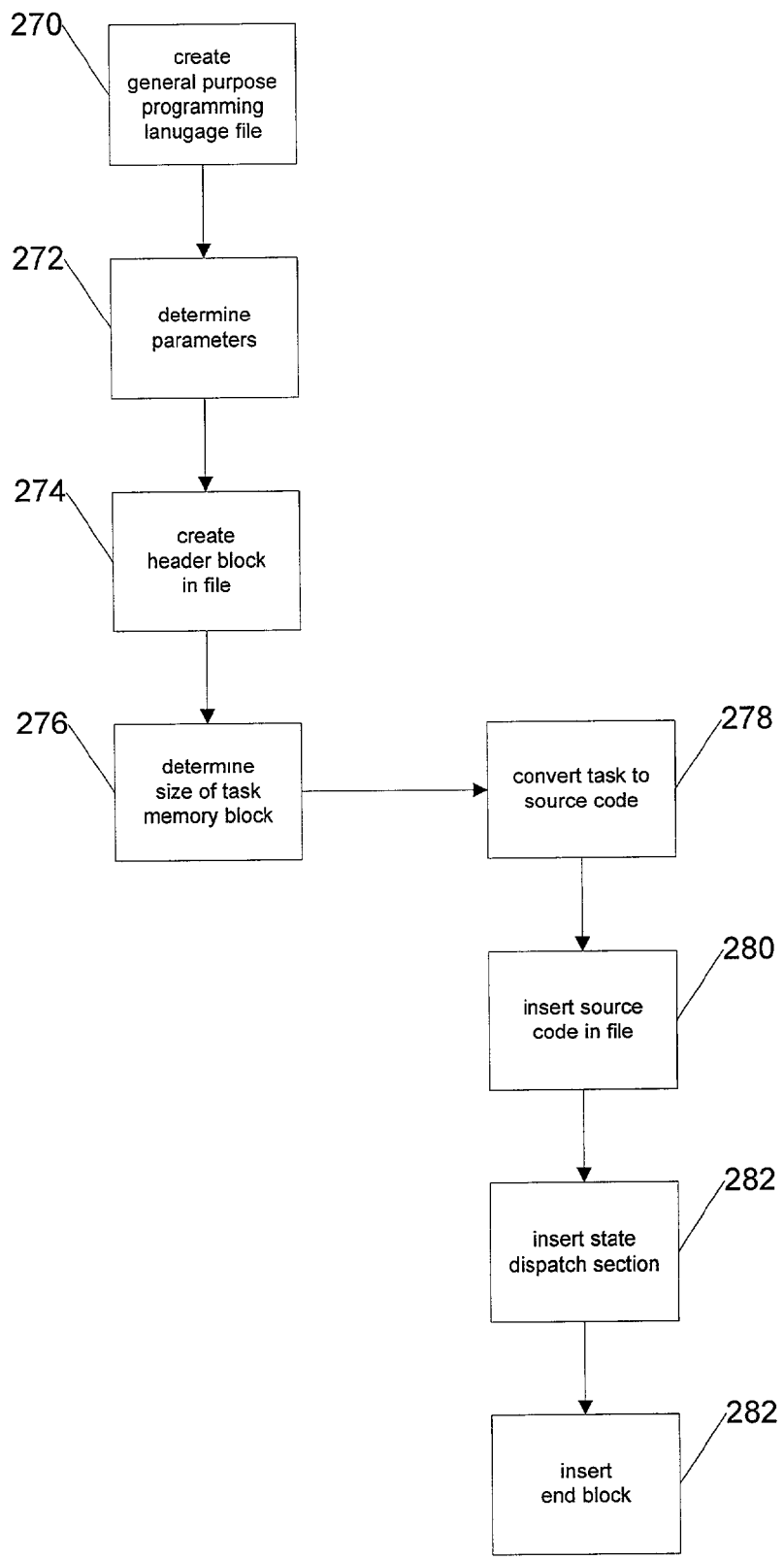
FIG. 11 is a flowchart illustrating an example process for translating a schedule into a task subroutine for a clinical trial simulation according to an embodiment of the present invention.

FIG. 11 is a flowchart illustrating an example process for translating a trial protocol schedule into a general purpose programming language task subroutine according to an embodiment of the present invention. Initially, the trial definition file is opened and a particular trial protocol schedule is obtained (step not shown). In step 270, a file is created that will house the general purpose programming language source code that corresponds to the particular trial protocol schedule.

Once the file has been created, the parameters for the file are determined, as illustrated in step 272. For example, the parameters include the set of variables or other data types that will be passed to the file. This may advantageously include any data needed by the particular protocol to carry out its function. Preferably, this allows the protocol to be flexible and allows the schedule to be modified in response to a subject's simulation, for example as may be desirable in a dose adjustment protocol.

Once the parameters have been determined, a header block is preferably created in the file that corresponds to the parameters, as shown in step 274. Additionally, the header block may include the various variables that may be used in the function. The set of variables used by the particular function can be important, depending on the high level programming language selected. For example, a high level programming language that employed dynamic allocation of memory space for locally declared variables or locally accessed global variables may not need to determine the size of the memory to be allocated.

In step 276, the size of memory block needed to execute the function is preferably determined. This size may vary, as explained above, depending on the types of variables used (local or global) and also on the type of general purpose high level programming language selected. Once the file has been created and the internal function has been declared with the header block, the tasks contained in the schedule can be converted into the high level programming language source code, as illustrated in step 278.

Preferably, after the source code has been generated, it can be inserted into the file, as shown in step 280. Once the code has been inserted, a state dispatch section may be inserted into the file, as seen in step 282. The state dispatch section preferably allows a subroutine to keep track of its place in execution between slices of execution time provided by the controller.

For example, a particular first function may execute for a time and then pause execution. During this pause, other functions may execute and when execution returns to the first function, it must determine where it left off during its previous execution phase. Advantageously, the state dispatch section allows the function to determine its previous state so that it may return to where it left off during its previous execution phase.

Once the state dispatch section has been inserted into the file, an end block may be inserted into the file and the file can be closed, as shown in final step 282. Preferably, the end block allows a function to completely exit after its task is complete. Additionally, the end block preferably sets a state variable for the function that indicates to the rest of the modules and functions in the trial simulation that the particular function's task is complete.

Figure 12:
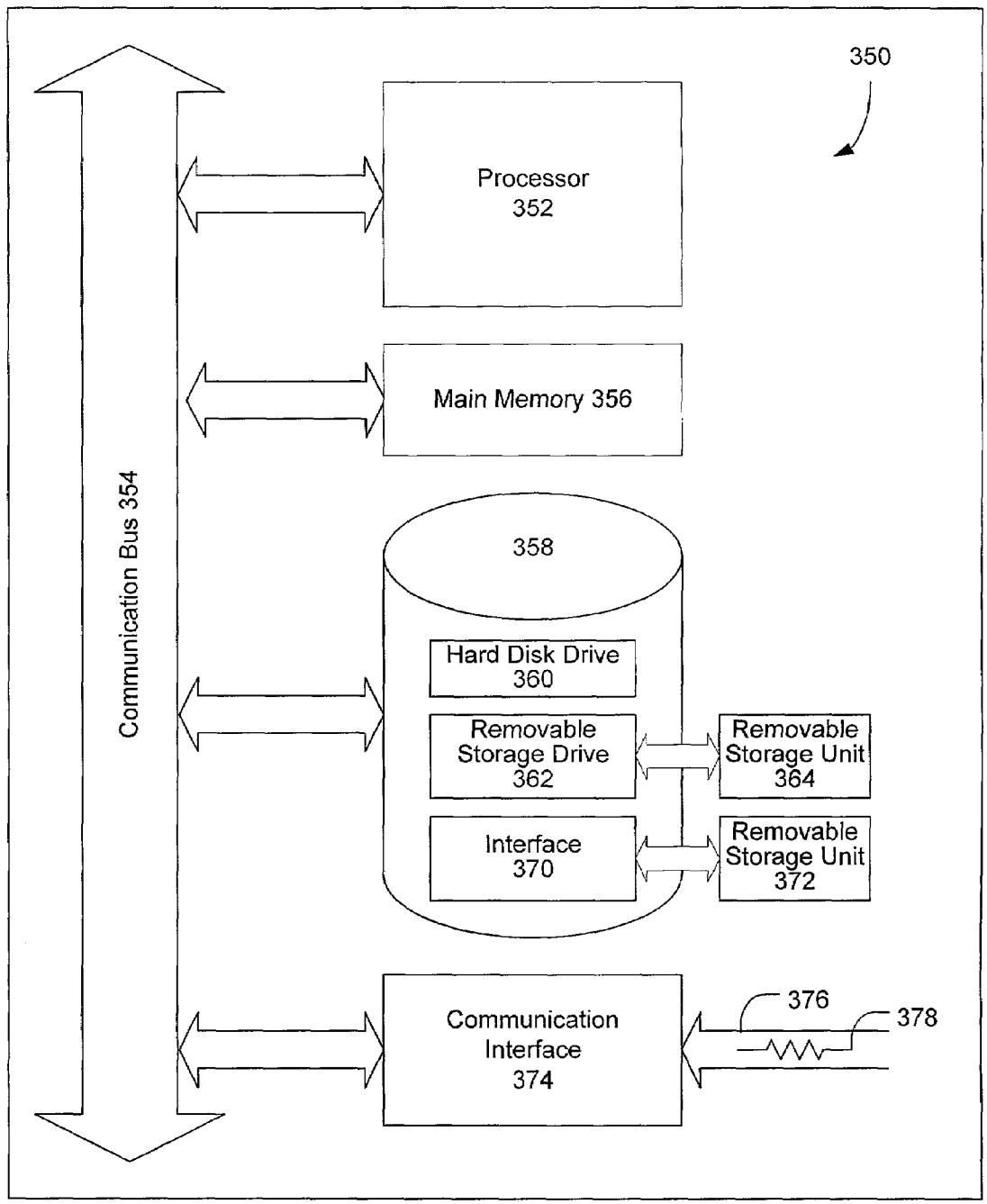
FIG. 12 is a block diagram illustrating an exemplary computer system as may be used in connection with various embodiments described herein.

FIG. 12 is a block diagram illustrating an exemplary computer system 350 that may be used in connection with various embodiments described herein. For example, the computer system 350 may be used in conjunction with [describe various uses for a general purpose computer in relation to the invention]. However, other computer systems and/or architectures may be used, as will be clear to those skilled in the art.

The computer system 350 preferably includes one or more processors, such as processor 352. Additional processors may be provided, such as an auxiliary processor to manage input/output, an auxiliary processor to perform floating point mathematical operations, a special-purpose microprocessor having an architecture suitable for fast execution of signal processing algorithms ("digital signal processor"), a slave processor subordinate to the main processing system ("back-end processor"), an additional microprocessor or controller for dual or multiple processor systems, or a coprocessor. Such auxiliary processors may be discrete processors or may be integrated with the processor 352.

The processor 352 is preferably connected to a communication bus 354. The communication bus 354 may include a data channel for facilitating information transfer between storage and other peripheral components of the computer system 350. The communication bus 354 further may provide a set of signals used for communication with the processor 352, including a data bus, address bus, and control bus (not shown). The communication bus 354 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

Computer system 350 preferably includes a main memory 356 and may also include a secondary memory 358. The main memory 356 provides storage of instructions and data for programs executing on the processor 352. The main memory 356 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, as well as read only memory (ROM).

The secondary memory 358 may optionally include a hard disk drive 360 and/or a removable storage drive 362, for example a floppy disk drive, a magnetic tape drive, an optical disk drive, etc. The removable storage drive 362 reads from and/or writes to a removable storage unit 364 in a well-known manner. Removable storage unit 364 may be, for example, a floppy disk, magnetic tape, optical disk, etc. which is read by and/or written to by removable storage drive 362. The removable storage unit 364 includes a computer usable storage medium having stored therein computer software and/or data.

In alternative embodiments, secondary memory 358 may include other similar means for allowing computer programs or other instructions to be loaded into the computer system 350. Such means may include, for example, a removable storage unit 372 and an interface 370. Examples of secondary memory 358 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage units 372 and interfaces 370, which allow software and data to be transferred from the removable storage unit 372 to the computer system 350.

Computer system 350 may also include a communication interface 374. The communication interface 374 allows software and data to be transferred between computer system 350 and external devices, networks or information sources. Examples of some types of components that might comprise communication interface 374 include a modem, a network interface (such as an Ethernet card), a communications port, a PCMCIA slot and card, and an infrared interface, to name a few. Communication interface 374 preferably implements industry promulgated protocol standards, such as Ethernet IEEE 802 standards, Fibre Channel, digital subscriber line (DSL), asymmetric digital subscriber line (ASDL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement non-standard interface protocols as well. Software and data transferred via communication interface 374 are generally in the form of signals 378 which may be electronic, electromagnetic, optical or other signals capable of being received by communication interface 374. These signals 378 are provided to communication interface 374 via a channel 376. This channel 376 carries signals 378 and can be implemented using wire or cable, fiber optics, a phone line, a cellular phone link, a radio frequency (RF) link, or other communications channels.

Computer programming instructions (i.e., computer programs or software) are stored in the main memory 356 and/or the secondary memory 358. Computer programs can also be received via communication interface 374. Such computer programs, when executed, enable the computer system 350 to perform the features relating to the present invention as discussed herein.

In this document, the term "computer program product" is used to refer to any media used to provide programming instructions to the computer system 350. Examples of these media include removable storage units 364 and 372, a hard disk installed in hard disk drive 360, and signals 378. These computer program products are means for providing programming instructions to the computer system 350.

In an embodiment that is implemented using software, the software may be stored in a computer program product and loaded into computer system 350 using hard drive 360, removable storage drive 362, interface 370 or communication interface 374. The software, when executed by the processor 352, may cause the processor 352 to perform the features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will be apparent those skilled in the relevant art. Various embodiments may also be implemented using a combination of both hardware and software.

Exemplary Embodiment

A non-limiting exemplary embodiment of translating a trial protocol into a compiled state machine will now be described. It is understood that this non-limiting exemplary embodiment description is presented as one of the various example embodiments of the claimed invention and is therefore not to be construed as limiting.

In one embodiment, the protocols for treatment and observation activities in a clinical trial can be highly variable. For example, a protocol may be defined as follows:

(a) Treatment schedule: Give X units of drug at 0800 hours and 2000 hours daily, for the duration of the subject's involvement in the trial.

(b) Observation schedule: Observe subject's blood pressure at 0930 hours on day 6 of subject's involvement in the trial, and every 7 days thereafter.

The above described trial protocol may then be translated into four separate schedules, namely TREATMENT, TREATMENT_DAILY, OBSERVATION, and OBSERVATION_DAILY. The protocols, as input into the trial simulator through a fixed form interface or a TDL interface are converted by a translator into the following format:

```
1.__    TREATMENT:
2.__        Let T1 be a variable denoting time in hours;
3.__        T1 = 0;
4.__        while subject is involved in trial
5.__        begin
6.__            wait until time T1;
7.__            Allocate a new task memory block for state machine
8.__            TREATMENT_DAILY, and add it to the queue.
9.__            T1 = T1 + 24;
10.__       end
11.__
12.__   TREATMENT_DAILY:
13.__       wait until 8 hours since midnight.
14.__       Administer X units of drug.
15.__       wait until 20 hours since midnight.
16.__       Administer X units of drug.
17.
18.__   OBSERVATION:
19.__       Let T1 be a variable denoting time in hours;
20.__       T1 = 6*24;
21.__       while subject is involved in trial
22.__       begin
23.__           wait until time T1;
24.__           Allocate a new task memory block for state machine
25.__           OBSERVATION_DAILY, and add it to the queue.
26.__           T1 = T1 + 7*24;
27.__       end
```

-continued

```
28.
29.__   OBSERVATION_DAILY:
30.__       wait until 9.5 hours since midnight.
31.__       Record subject's blood pressure.
32.
```

Additionally, each schedule is translated into a task subroutine in the source code for a general purpose high level programming language by the following rules:

1. Create a task subroutine having the same name as the schedule.
2. The subroutine has at least these arguments: TaskIdentifier, TaskMemoryBlock.
3. For each local variable in the schedule (such as T1), ensure that the TaskMemoryBlock contains space in which to store this variable.
4. Copy the pseudo-code of the schedule directly into the subroutine.
5. For each wait statement in the subroutine that says "wait until time t", replace it by the following four lines of code in the high-level language:
    TaskMemoryBlock.State = i;
    call enqueue(TaskIdentifier, t);
    return;
    L(i):
    where i is a state number (greater than 0) that is unique in the subroutine, and L(i) is a state label that is unique in the subroutine.
6. Create the State Dispatch Section at the beginning of the subroutine. For each unique state identifier i that was used in the subroutine, insert the following line at the beginning of the subroutine:
    if (TaskMemoryBlock.State = i) goto L(i);
    Then insert these lines after all of the if statements above:
    if (TaskMemoryBlock.State = −1) return;
    if (TaskMemoryBlock.State = 0) goto L(0);
    L(0):
7. At the end of the subroutine, insert these lines:
    TaskMemoryBlock.State = −1;
    return;

Applying these translation rules to the protocol schedules listed above results in the following task subroutines, which are presented in an algorithmic language. The numbers in parentheses at the end of each line indicates the corresponding line from the four schedules.

```
subroutine TREATMENT(TaskIdentifier, TaskMemoryBlock) (1)
begin (1)
        if (TaskMemoryBlock.State = 1) goto L1; (1)
        if (TaskMemoryBlock.State = 0) goto L0; (1)
        if(TaskMemoryBlock.State = −1) return; (1)
    L0: (1)
        TaskMemoryBlock.T1 = 0; (3)
        while (TaskMemoryBlock.T1 < Tend) (4)
        begin
            TaskMemoryBlock.State = 1; (6)
            call enqueue(TaskIdentifier, TaskMemoryBlock.T1); (6)
            return; (6)
        L1:(6)
            Allocate a memory block for task TREATMENT_DAILY, with State = 0,
            and assume its TaskIdentifier is newtid. (7)
            call enque(newtid, TaskMemoryBlock.T1); (8)
            TaskMemoryBlock.T1 = TaskMemoryBlock.T1 + 24; (9)
        end (10)
        TaskMemoryBlock.State = −1; (11)
        return; (11)
end (11)
subroutine TREATMENT_DAILY(TaskIdentifier, TaskMemoryBlock) (12)
begin
```

-continued

```
        if (TaskMemoryBlock.State = 1) goto L1; (12)
        if (TaskMemoryBlock.State = 2) goto L2; (12)
        if (TaskMemoryBlock.State = 0) goto L0; (12)
        if (TaskMemoryBlock.State = -1) return; (12)
    L0: (12)
        TaskMemoryBlock.T1 = T; (12)
        TaskMemoryBlock.State = 1; (13)
        call enqueue(TaskIdentifier, TaskMemoryBlock.T1 + 8); (13)
        return; (13)
    L1: (13)
        comment: this is an example of how we administer dose X to compartment A
        A = A + X; (14)
        TaskMemoryBlock.State = 2; (15)
        call enqueue(TaskIdentifier, TaskMemoryBlock.T1 + 20); (15)
        return; (15)
    L2: (15)
        A = A + X; (16)
        TaskMemoryBlock.State = -1; (17)
        return; (17)
end (17)
subroutine OBSERVATION(TaskIdentifier, TaskMemoryBlock) (18)
begin
        if (TaskMemoryBlock.State = 1) goto L1; (18)
        if (TaskMemoryBlock.State = 0) goto L0; (18)
        if (TaskMemoryBlock.State = -1) return; (18)
    L0: (18)
        TaskMemoryBlock.T1 = 6 * 24; (20)
        while (TaskMemoryBlock.T1 < Tend) (21)
        begin (22)
            TaskMemoryBlock.State = 1; (23)
            call enqueue(TaskIdentifier, TaskMemoryBlock.T1); (23)
            return; (23)
        L1: (23)
            Allocate a memory block for task OBSERVATION_DAILY,
            with State = 0, and assume its TaskIdentifer is newtid. (24)
            call enque(newtid, TaskMemoryBlock.T1); (25)
            TaskMemoryBlock.T1 = TaskMemoryBlock.T1 + 7 * 24; (26)
        end (27)
        TaskMemoryBlock.State = -1; (28)
        return; (28)
end (28)
subroutine OBSERVATION_DAILY(TaskIdentifier, TaskMemoryBlock) (29)
begin (29)
        if (TaskMemoryBlock.State = 1) goto L1; (29)
        if (TaskMemoryBlock.State = 0) goto L0; (29)
        if (TaskMemoryBlock.State = -1) return; (29)
    L0: (29)
        TaskMemoryBlock.T1 = T; (29)
        TaskMemoryBlock.State = 1; (30)
        call enqueue(TaskIdentifier, TaskMemoryBlock.T1 + 9.5); (30)
        return; (30)
    L1: (30)
        comment: this is an example of how we record blood pressure BP
        call WriteRecord(BP); (31)
        TaskMemoryBlock.State = -1; (32)
        return; (32)
end (32)
```

Alternatively, applying the translation rules to the protocol schedules listed above can result in the following task subroutines, which are presented in the Fortran language. The numbers in parentheses at the end of each line indicates the corresponding line from the four schedules. Importantly, the high level programming language employed may vary, as most general purpose high level programming languages offer similar sets of functionality that take advantage of the computing power of the computer running the clinical trial simulation.

```
subroutine TREATMENT(TaskIdentifier, TaskMemoryBlock) (1)
    integer TaskIdentifier (1)
    type (TREATMENTTaskMemoryBlock) TaskMemoryBlock (1)
```

-continued

```
    if(TaskMemoryBlock % State == 1) then goto 1001 (1)
    if(TaskMemoryBlock % State == 0) then goto 1000 (1)
    if(TaskMemoryBlock % State == -1) then return (1)
 1000 (1)
    TaskMemoryBlock % T1 = 0 (3)
    do while (TaskMemoryBlock % T1 < Tend) (4)
        TaskMemoryBlock % State = 1 (6)
        call enqueue(TaskIdentifier, TaskMemoryBlock % T1) (6)
        return (6)
 1001 (6)
        ! Allocate a memory block for task TREATMENT_DAILY,
        ! with State = 0, and assume its TaskIdentifer is newtid. (7)
        call enque(newtid, TaskMemoryBlock % T1) (8)
        TaskMemoryBlock % T1 = TaskMemoryBlock % T1 + 24 (9)
    end (10)
```

-continued

```
        TaskMemoryBlock % State = -1 (11)
        return (11)
end (11)
subroutine TREATMENT_DAILY(TaskIdentifier,
TaskMemoryBlock) (12)
    integer TaskIdentifier (12)
    type(TREATMENT_DAILYTaskMemoryBlock)
    TaskMemoryBlock (12)
    if(TaskMemoryBlock % State == 1) then goto 1001 (12)
    if(TaskMemoryBlock % State == 2) then goto 1002 (12)
    if(TaskMemoryBlock % State == 0) then goto 1000 (12)
    if(TaskMemoryBlock % State == -1) then return (12)
1000 (12)
    TaskMemoryBlock % T1 = T (12)
    TaskMemoryBlock % State = 1 (13)
    call enqueue(TaskIdentifier, TaskMemoryBlock % T1 + 8) (13)
    return (13)
1001 (13)
    ! this is an example of how we administer dose X to compartment A
    A = A + X (14)
    TaskMemoryBlock % State = 2 (15)
    call enqueue(TaskIdentifier, TaskMemoryBlock % T1 + 20) (15)
    return (15)
1002 (15)
    A = A + X (16)
    TaskMemoryBlock % State = -1 (17)
    return (17)
end (17)
subroutine OBSERVATION(TaskIdentifier, TaskMemoryBlock) (18)
    integer TaskIdentifier (18)
    type(OBSERVATIONTaskMemoryBlock) TaskMemoryBlock (18)
    if(TaskMemoryBlock % State == 1) then goto 1001 (18)
    if(TaskMemoryBlock % State == 0) then goto 1000 (18)
    if (TaskMemoryBlock % State == -1) then return (18)
1000 (18)
    TaskMemoryBlock % T1 = 6 * 24 (20)
    do while (TaskMemoryBlock % T1 < Tend) (21)
        TaskMemoryBlock % State = 1 (23)
        call enqueue(TaskIdentifier, TaskMemoryBlock % T1) (23)
        return (23)
1001 (23)
        ! Allocate a memory block for task OBSERVATION_DAILY,
        ! with State = 0, and assume its TaskIdentifer is newtid. (24)
        call enque(newtid, TaskMemoryBlock % T1) (25)
        TaskMemoryBlock % T1 =
        TaskMemoryBlock % T1 + 7 * 24 (26)
    end (27)
    TaskMemoryBlock % State = -1 (28)
    return (28)
end (28)
subroutine OBSERVATION_DAILY(TaskIdentifier,
TaskMemoryBlock) (29)
    integer TaskIdentifier (29)
    type(OBSERVATION_DAILYTaskMemoryBlock)
    TaskMemoryBlock (29)
    if(TaskMemoryBlock % State == 1) then goto 1001 (29)
    if(TaskMemoryBlock % State == 0) then goto 1000 (29)
    if(TaskMemoryBlock % State == -1) then return (29)
1000 (29)
    TaskMemoryBlock % T1 = T (29)
    TaskMemoryBlock % State = 1 (30)
    call enqueue(TaskIdentifier, TaskMemoryBlock % T1 + 9.5) (30)
    return (30)
1001 (30)
    ! this is an example of how we record blood pressure BP
    call WriteRecord(BP) (31)
    TaskMemoryBlock % State = -1 (32)
    return (32)
end (32)
```

While the particular system and method for simulating clinical trials with compiled state machines herein shown and described in detail is fully capable of attaining the above described objects of this invention, it is to be understood that the description and drawings represent the presently preferred embodiment of the invention and are, as such, a representative of the subject matter which is broadly contemplated by the present invention. It is further understood that the scope of the present invention fully encompasses other embodiments that may become obvious to those skilled in the art, and that the scope of the present invention is accordingly limited by nothing other than the appended claims.

What is claimed is:

1. A system for clinical trial simulation, comprising:
    an interface having a fixed form module and a trial definition language free form module, the interface configured to receive information that describes a trial protocol comprising a plurality of schedules for a clinical trial simulation and to receive information to dynamically modify trial schedules to simulate dosage adjustment protocols during trial in response to disease progression;
    a translator having a protocol parser and a code generator, the protocol parser configured to parse the trial protocol, the code generator configured to generate source code in a high level general purpose programming language;
    a compiler having a code parser and a machine code generator, the compiler configured to compile the generated source code into an executable program comprising a plurality of programmable state machines, each state machine corresponding to one of the plurality of schedules, the state machines dynamically determining dosage adjustment protocols and schedule parameters in response to information generated in simulation based on the disease progression; and
    a controller communicatively coupled with the interface, the translator, and the compiler, the controller configured to run the executable program including the plurality of programmable state machines, according to a time queue.

2. The system of claim 1, wherein the fixed form module is configured to receive trial protocol information conforming to a structured format.

3. The system of claim 2, wherein the free form module is configured to receive trial protocol information in a trial design language, conforming to a predefined structured language format designed for clinical trial simulation.

4. The system of claim 1, wherein the plurality of schedules comprises a dosing schedule.

5. The system of claim 1, wherein the plurality of schedules comprises an observation schedule.

6. A method for clinical trial simulation, comprising:
    receiving trial protocol information that describes a clinical trial simulation in a fixed form and a trial definition language free form;
    receiving information to dynamically modify trial schedules to simulate dosage adjustment protocols during trial in response to disease progression;
    arranging the trial protocol information into a plurality of schedules;
    translating the plurality of schedules into a high level general purpose programming language;
    compiling the translated plurality of schedules into an executable program comprising a plurality of state machines, each state machine corresponding to one of the plurality of schedules, the state machines dynamically determining dosage adjustment protocols and schedule parameters in response to information generated in simulation based on the disease progression; and executing the program including the plurality of state machines, according to a time queue as part of the clinical trial simulation.

7. The method of claim 6, wherein the receiving step comprises:
receiving trial protocol information that conforms to a structured format; and
receiving trial protocol information in a trial design language, conforming to a predefined structured language format designed for clinical trial simulation.

8. The method of claim 6, wherein the plurality of schedules comprises a dosing schedule.

9. The method of claim 6, wherein the plurality of schedules comprises an observation schedule.

10. A computer readable medium having stored thereon one or more sequences of instructions for causing one or more microprocessors to perform the steps for simulating a clinical trial, the steps comprising:
receiving trial protocol information that describes a clinical trial simulation in a fixed form and a trial definition language free form;
receiving information to dynamically modify trial schedules to simulate dosage adjustment protocols during trial in response to disease progression;
arranging the trial protocol information into a plurality of schedules;
translating the plurality of schedules into a high level general purpose programming language;
compiling the translated plurality of schedules into an executable program comprising a plurality of state machines, each state machine corresponding to one of the plurality of schedules, the state machines dynamically determining dosage adjustment protocols and schedule parameters in response to information generated in simulation based on the disease progression; and
executing the program as part of the clinical trial simulation including the plurality of state machines, according to a time queue.

11. The computer readable medium of claim 10, wherein the receiving step comprises:
receiving trial protocol information that conforms to a structured format; and
receiving trial protocol information in a trial design language, conforming to a predefined structured language format designed for clinical trial simulation.

12. The computer readable medium of claim 10, wherein the plurality of schedules comprises a dosing schedule.

13. The computer readable medium of claim 10, wherein the plurality of schedules comprises an observation schedule.

14. A system comprising a microprocessor, a persistent storage area, a volatile storage area and a communication means, the system including an execution area configured to simulate a clinical trial by performing the following steps:
receiving trial protocol information that describes a clinical trial simulation in a fixed form and a trial definition language free form;
receiving information to dynamically modify trial schedules to simulate dosage adjustment protocols during trial in response to disease progression;
managing the trial protocol information into a plurality of schedules, the plurality of schedules comprising a dosing schedule and an observation schedule;
translating each of the plurality of schedules into a high level general purpose programming language;
compiling the translated schedules into an executable program, comprising a plurality of programmable state machines, each state machine corresponding to a discrete one of the plurality of schedules, the state machines dynamically determining dosage adjustment protocols and schedule parameters in response to information generated in simulation based on the disease progression; and
executing the program as part of the clinical trial simulation including the plurality of state machines, according to a time queue.

15. The system of claim 1 wherein the translator operates according to a syntax and a structure of the trial protocol.

16. The system of claim 15 wherein the protocol parser is configured to determine a syntax and a structure of the trial protocol, to convert the trial protocol into an intermediate format, and to pass the intermediate format to the code generator.

17. The method of claim 6 wherein the trial protocol information is arranged into a plurality of schedules according to a syntax and a structure of the trial protocol information.

18. The method of claim 17 wherein the trial protocol information is analyzed to determine the syntax and structure.

19. The method of claim 10 wherein the trial protocol information is arranged into a plurality of schedules according to a syntax and a structure of the trial protocol information.

20. The method of claim 19 wherein the trial protocol information is analyzed to determine the syntax and structure.

* * * * *